(12) United States Patent
Amann et al.

(10) Patent No.: US 9,144,448 B2
(45) Date of Patent: Sep. 29, 2015

(54) MEDICAL INSTRUMENT AND MALE CONNECTOR FOR SAID INSTRUMENT

(71) Applicant: ERBE ELEKTROMEDIZIN GMBH, Tuebingen (DE)

(72) Inventors: Marcus Amann, Tuebingen (DE); Hansjoerg Bjoern Besch, Gomaringen (DE); Ralf Kuehner, Stuttgart (DE)

(73) Assignee: ERBE ELECTROMEDIZIN GMBH, Tuebingen (DE)

( * ) Notice: Subject to any disclaimer, the term of this patent is extended or adjusted under 35 U.S.C. 154(b) by 35 days.

(21) Appl. No.: 13/773,977

(22) Filed: Feb. 22, 2013

(65) Prior Publication Data

US 2013/0218150 A1  Aug. 22, 2013

(30) Foreign Application Priority Data

Feb. 22, 2012  (EP) .................................... 12156555

(51) Int. Cl.
*A61B 18/02* (2006.01)
*A61M 39/10* (2006.01)
*A61M 39/16* (2006.01)
*A61M 39/20* (2006.01)
*A61B 18/14* (2006.01)

(52) U.S. Cl.
CPC .............. *A61B 18/02* (2013.01); *A61M 39/105* (2013.01); *A61B 18/148* (2013.01); *A61M 39/165* (2013.01); *A61M 39/20* (2013.01); *A61M 2039/1083* (2013.01); *A61M 2039/1088* (2013.01)

(58) Field of Classification Search
None
See application file for complete search history.

(56) References Cited

U.S. PATENT DOCUMENTS

| 3,629,786 | A | * | 12/1971 | Reynolds et al. ............. 439/194 |
| 3,971,383 | A | | 7/1976 | van Gerven |
| 5,254,116 | A | | 10/1993 | Baust et al. |
| 5,520,682 | A | | 5/1996 | Baust et al. |
| 5,573,532 | A | | 11/1996 | Chang et al. |
| 7,137,978 | B2 | | 11/2006 | Levin |
| 2002/0089177 | A1 | | 7/2002 | Bonn |
| 2003/0028182 | A1 | | 2/2003 | Abboud et al. |
| 2004/0078033 | A1 | | 4/2004 | Levin |
| 2008/0319433 | A1 | | 12/2008 | Geiselhart |

FOREIGN PATENT DOCUMENTS

| CN | 101330880 A | 12/2008 |
| GB | 1 536 682 A | 12/1978 |
| WO | WO 99/65410 A1 | 12/1999 |
| WO | WO 2007/073810 A1 | 7/2007 |

\* cited by examiner

*Primary Examiner* — Brian T Gedeon
(74) *Attorney, Agent, or Firm* — Dickstein Shapiro LLP

(57) ABSTRACT

The medical instrument includes a male instrument connector, which includes at least one male fluid connector arranged on a flat face. A venting bore may also be arranged on the same face and disposed to act as pressure relief by which leaking fluids that accumulate in the instrument can be discharged. A cover cap may be attached to the face. The cover cap allows for sterilization of the instrument, including the male instrument connector.

14 Claims, 2 Drawing Sheets

MEDICAL INSTRUMENT AND MALE CONNECTOR FOR SAID INSTRUMENT

CROSS-REFERENCE TO RELATED APPLICATION

This application claims priority under 35 U.S.C. §119(a) to European Patent Application No. EP 12 15 6555.0, filed Feb. 22, 2012, which is incorporated by reference in its entirety.

TECHNICAL FIELD

Embodiments of the invention relate to a medical instrument, particularly, to the male connector of the instrument.

BACKGROUND

In practice, medical instruments having an instrument head that can be used by a surgeon or by any other person providing medical treatment to achieve physical effects on human or animal patients are known, such effects include, for example, the changing, dividing or ablating of tissue. Instruments are known, where the instrument head used must be supplied with a fluid, e.g., a cryogenic fluid, in order to bring about the desired physical effect. To accomplish this, the instrument head must include a supply line that connects the instrument head with a male instrument connector. The male instrument connector is adapted to a medical apparatus that supplies the instrument with the desired media, in particular fluids, as well as with electrical parameters. To this extent, the male instrument connector includes at least one male fluid connector that can be connected to a corresponding female connector on the apparatus. In addition, the male connector is usually rotation-symmetrically configured and includes a lateral venting opening, from which fluids that have the potential to become liberated due to leaks within the supply line can be discharged without risk. In doing so, undesirable effects such as, e.g., the inflation of a protective sleeve of the supply line, are prevented.

The male instrument connector must satisfy a multitude of requirements. For example, the fluids to be supplied to the instrument head are frequently under considerable pressure. These fluids must not escape in an uncontrolled manner. Likewise, a sudden pressure reduction of the fluids that are used can result in the development of extreme cold and thus in the risk of injuries. Therefore, conventional male instrument connectors are mostly manufactured of robust, complex rotating elements, which is expensive.

Furthermore, the sterilization of the instruments must be taken into consideration in instruments that are to be used more than once. In this case, the sterilization applies to all of the surfaces that are accessible from the outside. However, washing fluids, rinsing fluids, or the like must be prevented from penetrating into the fluid channels of the instrument because residues of such washing or rinsing fluids, should they remain in the instrument may lead to considerable disruptions of the instrument and ultimately can harm the patient.

SUMMARY

It is the object to be achieved by embodiments disclosed herein to provide an improved, cost-effective instrument that, on the one hand, is designed in a simple and non-confusing manner, and that, on the other hand, is easy to clean, and in particular, easy to sterilize.

The instrument in accordance with the disclosed embodiments include an instrument head that includes a grip and an application part that has at least one active component. This instrument head is supplied with at least one fluid in a gaseous, liquid or supercritical state of aggregation by a supply line. The fluid may be in a gaseous or liquid state, for example, carbon dioxide, nitrogen monoxide, argon, nitrogen, or any other fluid or fluid mixture. The supply line feeds this fluid to the instrument head. Optionally, an additional supply line is provided that feeds the fluid from the instrument head back to the male instrument connector. Arranged on the male instrument connector are—depending on the number of supply lines—one, two, or more male fluid connectors that are disposed to be in operative connection with corresponding female connectors provided on the medical apparatus in order to supply the instrument. As an alternative solution, it is also possible to swap the male fluid connectors on the male instrument connector side and the female connectors on the apparatus side with each other—i.e., the female fluid connectors may be provided on the male instrument connector, and the male fluid connectors may be provided on the apparatus. Such an arrangement is viewed as providing the same action and thus as being of equal technical validity. This arrangement can be used with each of the hereinafter described features and embodiments.

In one embodiment, the male instrument connector has a flat face on which the at least one male fluid connector is arranged. Furthermore, at least one venting opening is provided on the same flat face, which connecting the interior space of the jacket of the supply line with the environment. The jacket sheaths the fluid line.

If one of the fluid lines springs a leak along its length, or if the fluid in the instrument head escapes from the closed circuit of the fluid lines, this fluid will first enter the interior space of the jacket. The jacket—like the male connector itself and like the instrument head—is desirably hermetically sealed relative to the environment. However, this interior space is vented on the face of the male connector so that it is not possible for pressure to build in the jacket. Released fluid will freely flow off along the face of the male instrument connector. Thus, more serious damage to the instrument, as well as injuries to the patient and/or the surgeon, is avoided.

The arrangement of the at least one male instrument connector, as well as the venting opening on the face of the male connector, has a considerable effect on the sterilizability of the instrument, including its male connector. A cover cap can close the male fluid connector and the venting opening, so that no moisture, for example in the form of a washing fluid, rinsing fluid, soap or the like, can enter into the inner channels. In particular, this fluid ingress could have a particularly detrimental effect. If, for example, residues of washing or rinsing fluids were to obstruct the venting opening little-by-little, the venting opening may no longer protect in the case of a breakage or a leak of the fluid line. The disclosed embodiments will help prevent this.

Furthermore, the arrangement of several male fluid connectors on one and the same face allows a simple male connector design and the use of a large number of equal parts. The male fluid connector for the fluid supply, and at least one additional male fluid connector for the fluid discharge, may have a uniform design. The male fluid connectors may be arranged parallel to each other. The venting opening may be located between the male fluid connectors. The venting opening may be arranged on a shared line or also so as to deviate from a shared line. This male connector arrangement may be suitable for instruments including an application part that is rigid as well as for instruments with a flexible application part.

In one disclosed embodiment, the male instrument connector is configured as a flat plug. In another disclosed embodiment, the male instrument connector includes two housing shells that abut against each other along a joint. In doing so, the face may be configured so as to be without a joint. This makes for a particularly simple male connector assembly. The interior space encapsulated by the housing shells may be completely filled with a casting compound. As a result of this, the line connections located in the male connector are fixed in place and secured and any dead spaces that would have to be sterilized are avoided.

The male instrument connector may be associated with a cover cap which can be used to close the male fluid connectors. The cover cap may also cover the venting opening so that, during sterilization, it is not possible for fluids to enter into and remain in the inside channels, in particular, in the fluid lines and the interior space of the jacket.

BRIEF DESCRIPTION OF THE DRAWINGS

Additional details of exemplary embodiments are explained in greater detail below, with reference to the drawings, in which.

DETAILED DESCRIPTION

Figure 1:
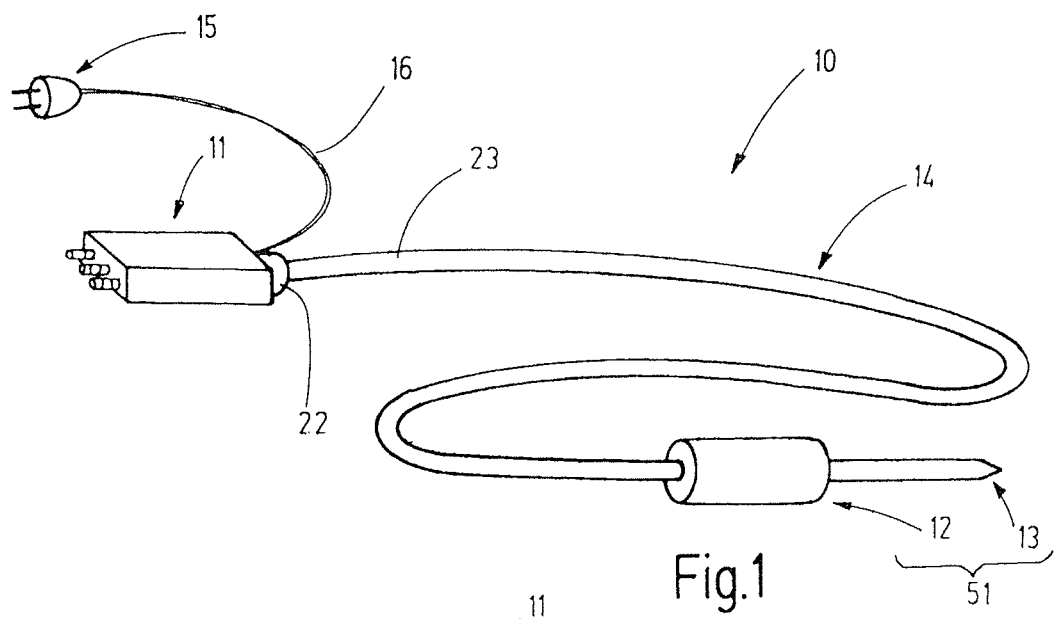
FIG. 1 shows a schematized perspective illustration of the instrument in accordance with a disclosed embodiment.

FIG. 1 shows a medical, in particular a surgical, instrument 10 that is intended for the connection to a medical apparatus (not shown). The instrument 10 includes an application part 51, which includes an instrument head 12 with an active part identified here, in general, as the tool 13, as well as a supply line 14 that connects the application part 51 with the male instrument connector 11. The tool 13 may be, for example, a cryogenic tool that can develop a desired effect, for example, a freezing effect, in at least one location. The required cryogenic fluid may be supplied via the male instrument connector 11. Optionally, it is possible to supply additional or other media, for example electrical current, e.g., RF current, or the like. In addition, another plug 15 may be connected to the male instrument connector 11 via a line 16 that continues through the supply line 14 and leads to the instrument head 12.

Figure 2:
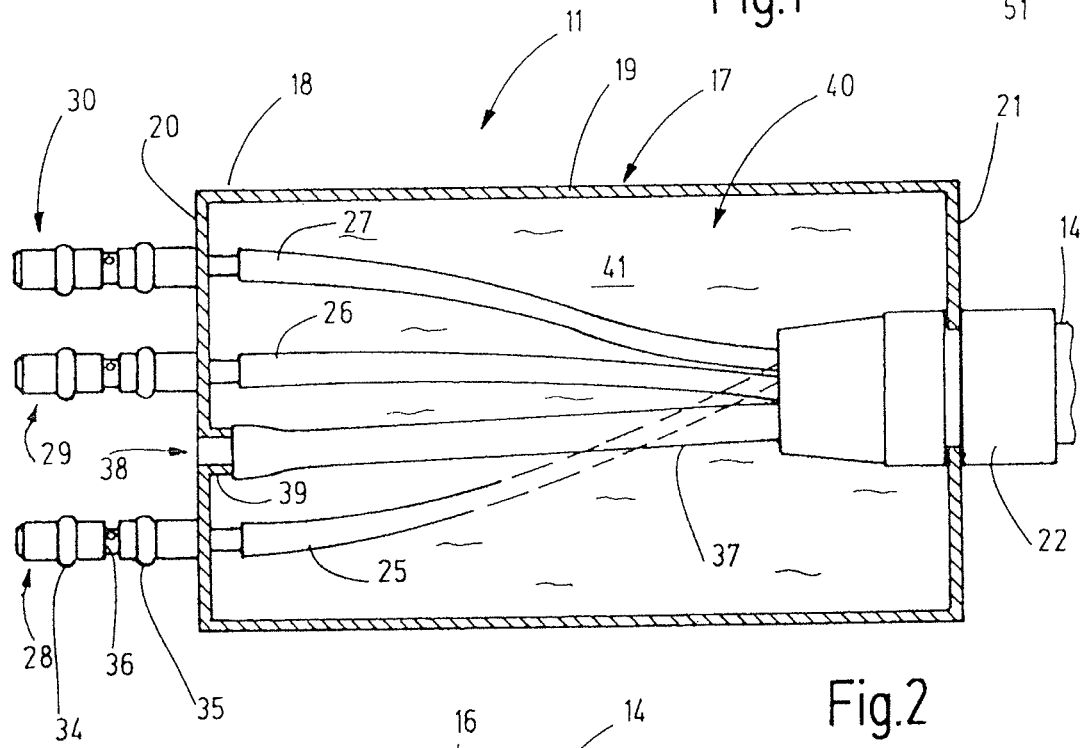
FIG. 2 shows a horizontal sectional view of the male instrument connector of the instrument of FIG. 1.
Figure 4:
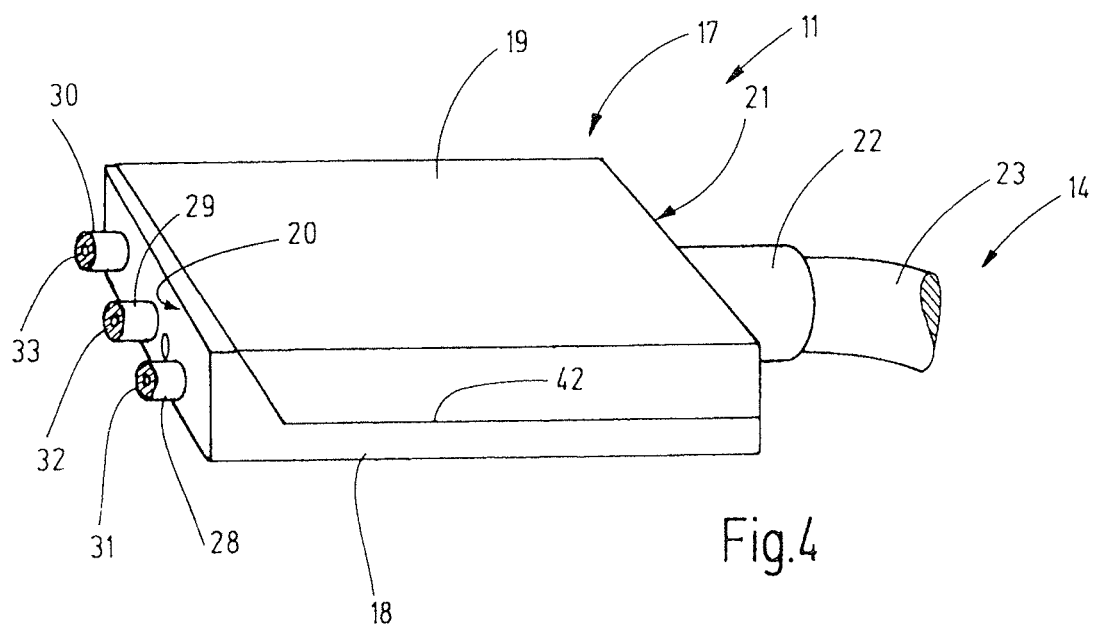
FIG. 4 shows a schematized perspective illustration of the male instrument connector of FIG. 1.

FIG. 2 is a schematic depiction of the internal design of the male instrument connector 11. The male instrument connector 11 includes a housing 17 that, desirably, includes several housing components, for example, two housing shells 18, 19, as can be seen in FIG. 4. For example, the housing is a flat housing that may be parallelepiped-shaped or another housing shape derived from that of a parallelepiped. The housing 17 may have a flat face 20 with lateral surfaces of the housing extending therefrom. The lateral surfaces may be oriented so as to be essentially at a right angle relative to the face 20. The lateral surfaces may be flat but also be slightly domed or be structured, e.g., have ribs, nubs or the like.

The supply line 14 is connected opposite the face 20 to the rear side 21 of the housing 17. This supply line 14 may include a fitting 22 in direct connection with the male instrument connector 11, for example in the form of a rubber grommet or the like. The fitting 22 desirably adjoins the peripheral surface of an outer jacket 23 of the supply line 14 so as to create a hermetic seal. The jacket 23 may be a flexible hose. The jacket 23 may have stiff sections or also be flexible along its entire length. In various embodiments, it may be made from one or more parts.

Figure 3:
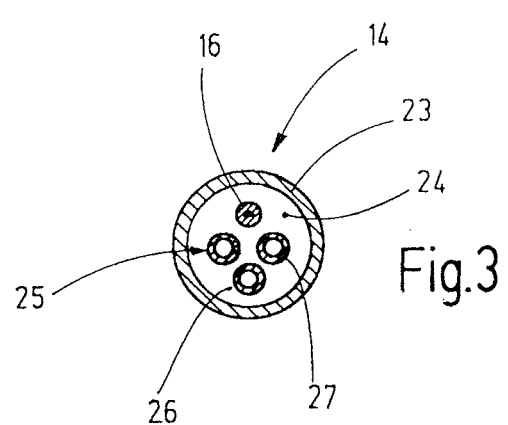
FIG. 3 shows a cross-section of the supply line of the instrument of FIG. 1.

As is shown in FIG. 3, in one embodiment, the jacket 23 encloses an interior space 24 that extends, without discontinuities, lengthwise through the hose forming the jacket 23 from the fitting 22 to the application part 51 or the instrument head 12 and communicates with the interior space—if present—of the instrument head 12. One or more fluid lines 25, 26, 27 may be arranged in the interior space 24 configured as flexible hoses. In addition, as mentioned above, the line 16 may extend through the supply line 14 and thus extend through the interior space 24. As is also shown in FIG. 3, the line 16 and the supply lines 25, 26, 27, do not completely fill the interior space 24. Rather, a certain free flow cross-section remains. This cross-section, however, may be substantially smaller than is shown in FIG. 3.

In one embodiment, the fluid lines 25, 26, 27 extend through the fitting 22 up to the oppositely arranged housing side where the fluid lines 25, 26, 27 are connected to the male fluid connectors 28, 29, 30. The male fluid connectors 28, 29, 30 are arranged on the face 20 and desirably extend at a right angle relative to the face 20 and, parallel to each other away from the face 20. Each of the male fluid connectors 28, 29, 30 has an internal channel 31, 32, 33, as is shown in FIG. 4. These channels 31, 32, 33 communicate with the internal channels of the fluid lines 25, 26, 27. In one embodiment, each of the male fluid connectors 28, 29, 30 is closed on the face side and is also cylindrical. In addition, in another disclosed embodiment, all of them have the same configuration.

In one exemplary embodiment, the male fluid connector 28 comprises two seals arranged at a distance from each other in axial direction, for example O-rings 34, 35 that are seated in matching annular O-ring grooves. Between these, the internal channel 31 communicates with at least one radial bore 36 that may be provided in a slightly recessed radial groove. In one embodiment, the two O-rings 34, 35 have the same outside diameter that is adapted to the inside diameter of the bore 44. If the male fluid connector 28 is inserted into the bore (e.g., 44) and if pressurized fluid is supplied through the fluid line 52, a pressure-supported inhibition of the male fluid connector 28 in the bore 44 is created due to the same outside diameters of the O-rings 34, 35. Different outside diameters of the O-rings are able to influence the effective engagement of the male fluid connector 28 in the bore 44. The above description of the male fluid connector 28 applies correspondingly to that of the male fluid connectors 29 and 30.

The interior space 24 of the supply line 14 ends either in or at the fitting 22. A venting hose 37 or a corresponding tube connects the interior space 24 with a venting opening 38 on the face 20, the venting opening 38 having the form of a venting bore that is disposed to provide a pressure relief inside the interior space 24 and to communicate directly or, by means of a connection with the apparatus, with the atmosphere. An inward-projecting extension 39 formed on the face 20 may be provided on the venting bore 38, whereby the venting hose 37 is seated on the extension.

The housing 17 encapsulates an interior space 40 that may be completely filled with the casting compound 41. In doing so, the casting compound 41 encloses the fluid lines 25 through 27, as well as the venting hose 37 and the part of the fitting 22 located in the housing 17. The fitting 22 is fixed in place and sealed relative to the interior space 40. Also, a housing joint 42 existing between the housing shells 18, 19 is sealed by the casting compound 41. The housing joint 42 may be located outside the face 20 so that the latter is without discontinuities.

The instrument 10 that has been described so far may be provided, for example, as a one-way instrument. When in use, its male instrument connector 11 is secured in an appropriate slot of an apparatus intended for supply. In doing so, the male fluid connectors 28, 29, 30 enter the corresponding female connectors of the apparatus. For example, the male fluid connector 29 receives a suitable fluid via its associate female connector, for example liquid nitrogen that, e.g., is conveyed through the fluid line 26 through the supply line 14 to the instrument head 12. Used fluid, for example evaporated and thus gaseous nitrogen, moves through at least one of the two fluid lines 25, 27 back to at least one of the male fluid connectors 28, 30 and is again received there by the apparatus. The liquid nitrogen that is at the same time supplied to the instrument head 12 and, in particular, to the tool 13 may, for example, evaporate in the tool 13 for cryogenic applications and, in doing so, absorb heat, the heat being transported away with the gaseous nitrogen via the fluid lines 25, 27. In doing so, the corresponding fluid—in this case nitrogen, for example—does not leave the circuit formed by the fluid lines 25, 26, 27 and the instrument head 12.

However, should a leak occur at any point, the fluid that is used, for example liquid of gaseous nitrogen, may enter the interior space 24 of the supply line 14. Even if liquid nitrogen were to enter in only very minute amounts into this interior space 24, the nitrogen would significantly inflate the interior space 24 in an instant as a result of the volume increase resulting from evaporation if the space were closed toward the outside. The same would take place if fluids were conveyed under high pressure through the fluid lines 25, 26, 27. However, in the disclosed embodiments, such leaking fluids could not cause a pressure stasis. Rather, the fluids would be discharged toward the outside via the venting hose 37 and the venting bore 38. To accomplish this, the apparatus-side slot could have an additional opening in alignment with the venting bore 38.

Figure 5:
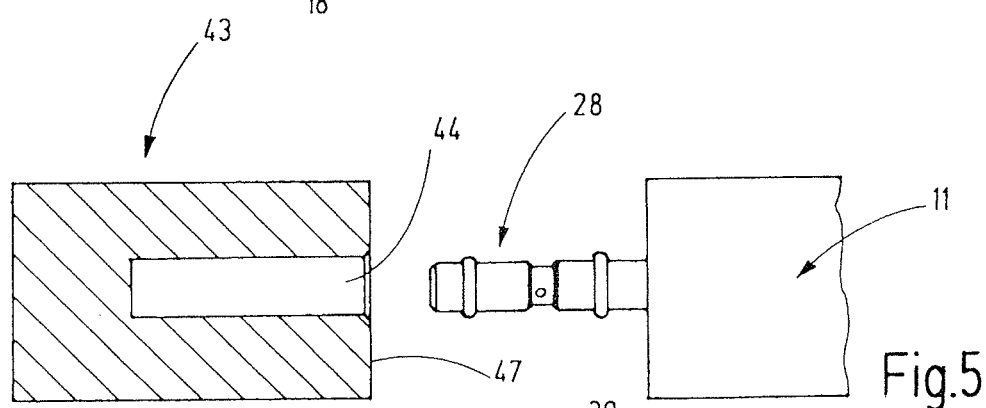
FIG. 5 shows a basic diagram of the male instrument connector and its cap, vertically in section.
Figure 6:
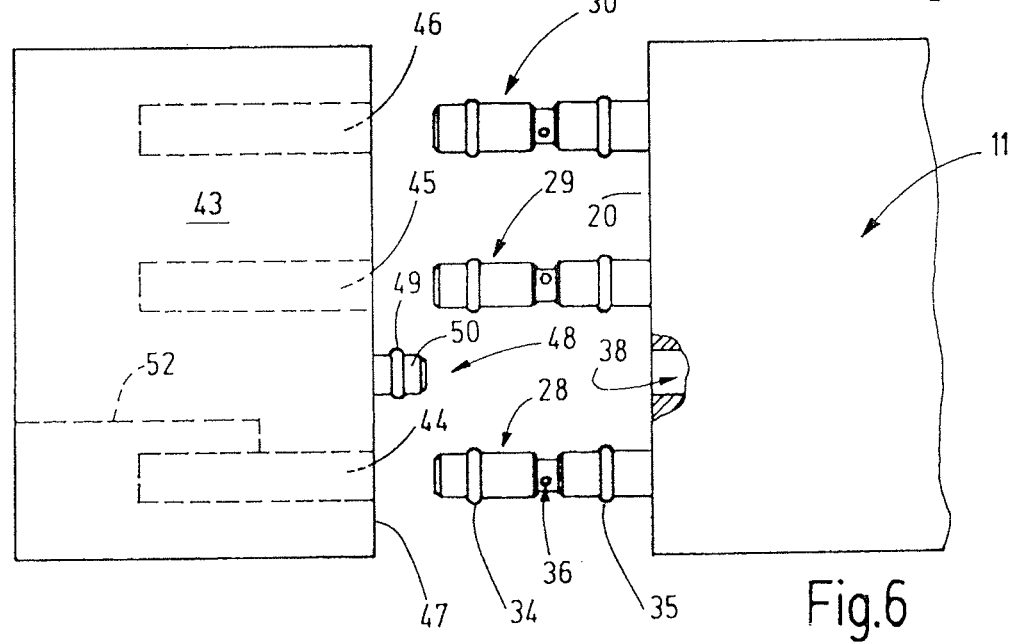
FIG. 6 shows a plan view of the male instrument connector and the cover cap.

The instrument 10 of the disclosed embodiments may also be designed as a multi-use, sterilizable instrument. In this case, it may be provided with a cover cap 43 as is shown in FIGS. 5 and 6. This cap has one bore 44, 45, 46, respectively, for each of the male fluid connectors 28, 29, 30, the positions of the bores 44, 45, 46 corresponding to the positions of the male fluid connectors 28, 29, 30. The bores 44, 45, 46 may have a cylindrically closed wall against which abut the respective gaskets 34, 35 so as to create a seal. In this manner, the radial bores 36 and thus the channels 31, 32, 33 are sealed. The bores 44, 45, 46 may extend from a flat face 47 of the cover cap 43 parallel to each other into the body of the cover cap 43.

In addition, a suitable sealing means 48 may be provided for the venting bore 38 on the face 47, as can be seen in FIG. 6. For example, this sealing means 48 may be a nipple 50 provided with a gasket 49. This nipple 50 may fit into the venting bore 38 so that the gasket 49 abuts against the inside wall of the venting bore 38 so as to create a seal when the face 47 of the cover cap 43 abuts against the face of the male instrument connector 11.

For sterilization of the instrument 10, the cover cap 43 is connected to the male instrument connector 11 in such a manner that all the male fluid connectors 28, 29, 30 are seated in the respective bores 44, 45, 46 and that the venting bore 38 is closed by the sealing means 48. In order to create a secure connection between the cover cap 43 and the male instrument connector 11 the cover cap 43 and the male instrument connector 11 may have complementary connecting means (not illustrated) in the form of a groove and spring or a hook and eye, or the like. When the cap is connected, a sterilization can be performed by washing, rinsing and the action of other fluids such as, for example, steam, and any penetration of detergents or other substances into the interior of the fluid lines 25, 26, 27 and, in particular, in the interior space 24, is precluded.

The male instrument connector 11 in accordance with FIG. 4 may be connected to differently designed surgical instruments. In doing so, a distinction is made between the so-called rigid probes and flexible probes. A rigid probe comprises a rigid, pressure-resistant application part 51 that is configured, for example, for pressures of up to 65 bar. In order to ensure such pressure resistance, each of the fluid-conveying parts, as well as each of the connecting means of an application region 51 such as, for example, a capillary tube, a cover cap, a flange, a nut and a sealing means in the form of O-rings must be configured so as to be pressure-resistant. From an engineering viewpoint, it is currently still very difficult to produce these fluid-conveying parts, as well as the connecting means, in the necessary small dimensions such that they display pressure resistance and flexibility. In order to prevent a flexible probe comprising an application part 51 that is not designed to be pressure-resistant from being supplied with too high a pressure, the supply apparatus features several different connections in the form of the bores 44, 45, 46. For example, the bore 46 may be configured as a port for the fluid return of a rigid probe. Then a high pressure may be applied on the apparatus side of this port. To this extent, the bore 45, for example, may be configured for the connection of a flexible probe, in which case it would not be possible to apply high pressure on the apparatus side. In a male instrument connector 11 configured in this manner, the male fluid connector 28 that is in operative connection with the bore 44 is configured as a fluid supply port and is used by a rigid probe as well as by a flexible probe.

To this extent, the male fluid connector 30 is used for returning the fluid from a rigid probe, and the male fluid connector 29 is used for the return of the fluid from a flexible probe.

The exemplary embodiment of the male instrument connector 11 as shown by FIGS. 2 and 6 is a basic embodiment of such a connector. If, for example, a male instrument connector 11 is configured for use with a rigid probe, there may be, for example, no fluid line 27 and no male fluid connector 30. Instead, the respectively configured male instrument connector 11 has a closure means at the location where the male fluid connector 30 would otherwise be provided in order to close the housing 17. Consequently, it is still possible to fill the interior space 24 of the housing 17 with the casting compound 41. If the fluid line 26 and the male fluid connector 29 are omitted in a configuration of a flexible probe, a closure means is used instead of the male fluid connector 29 in order to allow filling of the male instrument connector 11.

The instrument in accordance with the present disclosure includes a male instrument connector 11 that includes male fluid connectors 28, 29, 30. The male fluid connectors 28, 29, 30 may be arranged on a flat face 20. A venting bore 38 may also be arranged on the same face 20, disposed to act as pressure relief for leaking fluids that have accumulated in the instrument 14, in particular leaking gases, can be discharged toward the outside. This concept allows the optional provision of a cover cap 43 that is attached to the face 20. The cover cap allows sterilization of the instrument 10, including the male instrument connector 11.

What is claimed is:

1. A medical instrument, comprising:
    an instrument head;
    a supply line that comprises a fluid line for supplying a fluid and a jacket, the fluid line extending through an interior space of the jacket;
    a male instrument connector that has a face;
    a male fluid connector in fluid communication with the fluid line and arranged on the face of the male instrument connector; and
    at least one venting opening in communication with the interior space of the jacket and arranged on the face of the male instrument connector,
    wherein the male instrument connector has an interior space that is completely filled with a casting compound.

2. The instrument of claim 1, wherein the supplied fluid is at a pressure that is greater than ambient pressure.

3. The instrument of claim 1, wherein the supply line is flexible.

4. The instrument of claim 1, wherein the male instrument connector is a flat plug that is delimited by flat sides oriented at a right angle relative to the face.

5. The instrument of claim 1, wherein the male instrument connector comprises two housing shells that abut against each other at a joint.

6. The instrument of claim 1, wherein the face of the male instrument connector is without joints.

7. The instrument of claim 1, wherein the male fluid connector is tubular and closed at a face end and has an internal channel in communication with a radial bore.

8. The instrument of claim 7, wherein the male fluid connector has gaskets on both sides of the radial bore.

9. The instrument of claim 1, wherein the male instrument connector is associated with a cover cap adjoining the face.

10. The instrument of claim 9, wherein the cover cap is configured to close the male fluid connector and the at least one venting opening.

11. The instrument of claim 1, wherein the supply line comprises at least two fluid lines that extend through the interior space of the jacket, one of the at least two lines conveying the fluid to the instrument head and the another of the at least two lines conveying the fluid away from the instrument head.

12. The instrument of claim 11, wherein at least two male fluid connectors are arranged on the face, the at least two male fluid connectors communicating with the at least two fluid lines and being aligned parallel to each other and at a right angle relative to the face.

13. The instrument of claim 12, wherein each of the at least two male fluid connectors have the same configuration as each other of the at least two male fluid connectors.

14. The instrument of claim 12, wherein the at least one venting opening is located between two of the at least two male fluid connectors.

* * * * *